(12) United States Patent
Seifert et al.

(10) Patent No.: US 8,486,859 B2
(45) Date of Patent: Jul. 16, 2013

(54) USE OF RIBOSE TO ENHANCE PLANT GROWTH

(75) Inventors: John G. Seifert, St. Cloud, MN (US); Linda M. Shecterle, Minneapolis, MN (US)

(73) Assignee: Bioenergy, Inc., Ham Lake, MN (US)

( * ) Notice: Subject to any disclaimer, the term of this patent is extended or adjusted under 35 U.S.C. 154(b) by 880 days.

(21) Appl. No.: 10/147,100

(22) Filed: May 15, 2002

(65) Prior Publication Data

US 2003/0217577 A1    Nov. 27, 2003

(51) Int. Cl.
*A01N 57/00* (2006.01)
*A61K 31/545* (2006.01)
*A61K 31/44* (2006.01)

(52) U.S. Cl.
USPC ........... 504/113; 504/114; 504/115; 504/189; 504/209; 504/291; 504/294

(58) Field of Classification Search
USPC ................. 504/113–115, 189, 209, 291, 294, 504/299; 514/23–62
See application file for complete search history.

(56) References Cited

U.S. PATENT DOCUMENTS

| | | | |
|---|---|---|---|
| 5,310,665 A | | 5/1994 | Lambeir et al. |
| 5,366,954 A | | 11/1994 | Bestwick et al. |
| 5,459,121 A | * | 10/1995 | Shin et al. ............ 504/114 |
| 5,549,729 A | * | 8/1996 | Yamashita ............ 71/26 |
| 5,797,976 A | | 8/1998 | Yamashita |
| 6,309,440 B1 | | 10/2001 | Yamashita |
| 2002/0121046 A1 | * | 9/2002 | Yamashita ............ 47/58.1 |

FOREIGN PATENT DOCUMENTS

JP    02255603 A  *  10/1990

OTHER PUBLICATIONS

Mitsui et al, Dynamic Studies on the Nutrient Uptake by Crop Plants. XXI. The Significance of Carbohydrate Metabolism on, Potassium Uptake, Especailly Compared with Phosphate Uptake by Rice Plants, 1959, Nippon Dojo Hiyogaku Zasshi, vol. 30, pp. 263-268. (Abstract only.).*
"Arabinose" [online]. Wikipedia® [retrieved on Mar. 31, 2008]. Retrieved from the internet <URL:http://en.wikipedia.org/wiki/Arabinose>; 1 page. Last modified Jan. 3, 2008.
"Deoxyribose" [online]. Wikipedia® [retrieved on Mar. 31, 2008]. Retrieved from the internet <URL:http://en.wikipedia.org/wiki/Deoxyribose>; 3 pgs. Last modified Feb. 11, 2008.
Elsheikh et al., "Effects of *Rhizobium* inoculation, organic and chemical fertilizers on yield and physical properties of faba bean seeds," *Plant Foods for Human Nutrition*, Jun. 1997;51:137-144.
Huner et al., "The effects of low temperature acclimation of winter rye on catalytic properties of its ribulose biphosphate carboxylase-oxygenase," *Can. J. Biochem*, 1979;57:1036-1041.
Lampen, "Formation of Ribose Phosphate from Xylose by Extracts of *Lactobacillus pentosus*," *The Journal of Biological Chemistry*, Oct. 1953;204:999-1010.
"Lyxose" [online]. Wikipedia® [retrieved on Mar. 31, 2008]. Retrieved from the internet <URL:http://en.wikipedia.org/wiki/Lyxose>; 1 page. Last modified Mar. 10, 2008.
Omer et al., "Effect of cutting, phosphorus and potassium fertilization on guar plant (*Cyamoposis tetragonoloba*) in newly reclaimed soil in Egypt," *Plant Foods for Human Nutrition*, Nov. 1993;44:277-284.
"Photosynthesis" [online]. Microsoft® Encarta® Online Encyclopedia 2007 [retrieved on Apr. 8, 2008]. Retrieved from the internet <URL:http://encarta.msn.com/text_761572911_0/Photosynthesis.html>; 4 pgs.
"Ribose" [online]. Wikipedia® [retrieved on Feb. 7, 2008]. Retrieved from the internet <URL:http://en.wikipedia/org/wiki/Ribose>; 2 pgs. Last modified Jan. 16, 2008.
"Ribose*PLUS*" datasheet [online]. BioActive Nutrients, © 1999-2006 [retrieved on Mar. 13, 2008]. Retrieved from the Internet:<URL:http://www.bioactivenutrients.com/ribose.html>; 2 pgs.
"Ribulose" [online]. Wikipedia® [retrieved on Mar. 31, 2008]. Retrieved from the internet <URL:http://en.wikipedia.org/wiki/Ribulose>; 1 page. Last modified Mar. 10, 2008.
Tinus et al., "Relationship between carbohydrate concentration and root growth potential in coniferous seedlings from three climates during cold hardening and dehardening," *Tree Physiology*, Oct. 2000;20:1097-1104.
"Xylitol" [online]. Wikipedia® [retrieved on Feb. 7, 2008]. Retrieved from the internet <URL:http://en.wikipedia.org/wiki/Xylitol>; 5 pgs. Last modified Jan. 17, 2008.
"Xylose" [online]. Wikipedia® [retrieved on Mar. 31, 2008]. Retrieved from the internet <URL:http://en.wikipedia.org/wiki/Xylose>; 1 page. Last modified Mar. 5, 2008.
"Xylulose" [online]. Wikipedia® [retrieved on Mar. 31, 2008]. Retrieved from the internet <URL:http://en.wikipedia.org/wiki/Xylulose>; 1 page. Last modified Mar. 12, 2008.
"Carbohydrate," Wikipedia [online]. [retrieved on Jan. 5, 2010]. <URL:http://en.wikipedia.org/wiki/Carbohydrate>; 8 pgs. (Page last modified Jan. 1, 2010).
"Pentose," Wikipedia [online]. [retrieved on Jan. 5, 2010]. <URL:http://en.wikipedia.org/wiki/Pentose>; 2 pgs. (Page last modified Dec. 18, 2008).
"Sugar alcohol," [online] [retrieved on Jan. 5, 2010]. <URL:http:en.wikipedia.org/wiki/Sugar_alcohol>; 2 pgs. (Page last modified Jan. 2, 2010).
Tomo et al., "Evaluation of Several Saccharides As Osmotic Agent for Peritoneal Dialysate," *Peritoneal Dialysis International*, 2000; 20:727-733.

* cited by examiner

*Primary Examiner* — Renee Claytor
(74) *Attorney, Agent, or Firm* — Mueting, Raasch & Gebhardt, P.A.

(57) ABSTRACT

The present invention relates to methods and compositions for supplementing the soil/diet of plants in order to enhance plant growth, yield, hardening, as well as the recovery of plants which undergo transplantation. The present invention provides ribose and other pentose sugars and their derivatives, alone or in combination with other carbohydrates, electrolytes, minerals, enzymes, micronutrients, macronutrients, or other ingredients to enhance plant growth, yield, hardening, and aid in the recovery during and following transplantation.

12 Claims, 4 Drawing Sheets

USE OF RIBOSE TO ENHANCE PLANT GROWTH

FIELD OF INVENTION

The present invention relates to methods and compositions for treating plants in order to enhance the growth and yield of plants, hardiness, as well as aiding in a plants recovery during and following a transplant shock incidence. The methods and compositions of the invention are suitable for topical application and are useful in increasing the rate of growth of plants, increasing the yield, hardening of the plants, and aiding in the recovery of plants during and following transplantation.

BACKGROUND OF THE INVENTION/RELATED ART

Plants depend on light and carbon dioxide to produce the simple sugar, glucose. The produced glucose is then used as the energy source to build the leaves, flowers, fruits, and seeds of the plant. Plant growth and product yield are important factors in the horticulture business. In order to maximize the potential of each plant the "ideal" growing environment must be created. Creating the "ideal" environment is often a process that is not feasible to many growers. Therefore, fertilization with natural and artificial substances plays an important role.

In the area of plant fertilization many compounds have been used, including nitrogen, phosphorus, potassium as well as others. Effective fertilization can play a critical role in the growth of plants and is frequently the determining factor in the quality and quantity of the outcome. Past research has investigated which fertilizers or combinations thereof promote the optimal growth of the plant. For example, it has been shown that fertilization with nitrogen increased plant growth and yield, in addition to improving seed quality and nutritional value[1]. Further, another study demonstrated that phosphorus fertilization can significantly increase plant weight, seed yield, seed mucilage content, and seed protein content[2]. In the same study, fertilization with a combination of phosphorus and potassium resulted in the highest seed yield, seed mucilage content, and seed protein content[2]. Fertilization of plants with a combination of nitrogen, phosphorus, and potassium is so widely recognized that the concentration of each is printed on the label of many (if not all) plant fertilization products.

New findings in the area of fertilization are of great interest. For example, it is unknown to what extent various additives maybe substituted for, replace, show synergistic effects or interfere with the benefit derived from a fertilizer given alone. This is the main motivator for pursuing the investigations leading to this invention.

All commercially grown plants (potted plants, annuals, shrubs, trees, etc) are exposed to transplant shock during their existence, as well as hardening during re-implantation of a plant. The term transplant shock is usually reserved for replanted annual plants; however, it is not exclusive to this state, and can cover anything from severe wilting to healthy-looking plants with a mysterious reluctance to resume growth after transplantation. The suspected cause of transplant shock is the failure of the plant to root well or a diminished root system (due to removal from its original site) and consequently the plant becomes poorly established in the new landscape soil. The plant can incur additional stress/shock following transplantation from lack of sufficient nutrients and/or water requirements following re-implantation into the soil.

The period of slow growth following transplantation will vary from species to species of the variety of plants. For example, it is not uncommon for a large tree to experience a period of stagnant growth for several years following transplantation due to inadequate initial conditions or continual absence of key nutrients.

During transplantation of plants, much of the plant's root system is often left behind during the harvestation of the desired plant. Once re-implanted, the reduced root system is unable to supply an adequate amount of nutrients, as well as a necessary root arrangement, and water for adequate normal growth. The increase and decrease of root growth potential paralleled the rise and fall of carbohydrate concentrations in the roots, not reflecting the subsequent stem evolution.

Hardening of a plant is also important during and following transplantation. Hardening relates to the acclimation to cold temperatures and/or inclement weather patterns. Tinus et al. (2000) reported a close correspondence between the level of cold hardiness and absolute concentration of sugars.[3] Cold does not merely mean sub-thermal temperatures, but does reflect the change in state that a plant experiences when it is plucked from its normal inhabitant into a climate of different conditions. The increase and decrease of root growth potential paralleled the rise and fall of carbohydrate concentration in the roots, not reflecting the subsequent stem evolution. As temperatures drop, sugars tend to concentrate and then decrease in concentration. Upon this decrease in sugar availability, the plant turns to a dormancy state. Enzyme activity of the plant is also maintained when sugars are available, providing that the environmental conditions are acceptable. As temperature decreased, enzyme activity also decreased. However, enzyme patterns may be maintained with adequate substrate base. The combination of optimal enzyme patterns and substrate bases would ensure an ideal condition for the plant to accept and subsequently maintain or enhance its root/stem growth, leading to a more prolific plant.[4]

Further, not only does the addition of ribose, other pentose sugars, their derivatives, or a combination of pentose sugars with other nutrients aid in the above, but has additional factors in providing aided features in hardening of essential fundamental parts of the plant, necessary in its initial and continual growth, such as roots, stem, and shoot characteristics.

SUMMARY OF THE INVENTION

The present invention relates to methods and compositions for supplementing the soil/diet of plants in order to enhance plant growth, yield, hardening, as well as the recovery of plants which undergo transplantation. The present invention provides ribose and other pentose sugars and their derivatives, alone or in combination with other carbohydrates, electrolytes, minerals, enzymes, micronutrients, macronutrients, or other ingredients to enhance plant growth, yield, hardening, and aid in the recovery during and following transplantation.

DETAILED DESCRIPTION OF THE INVENTION

Figure 1:
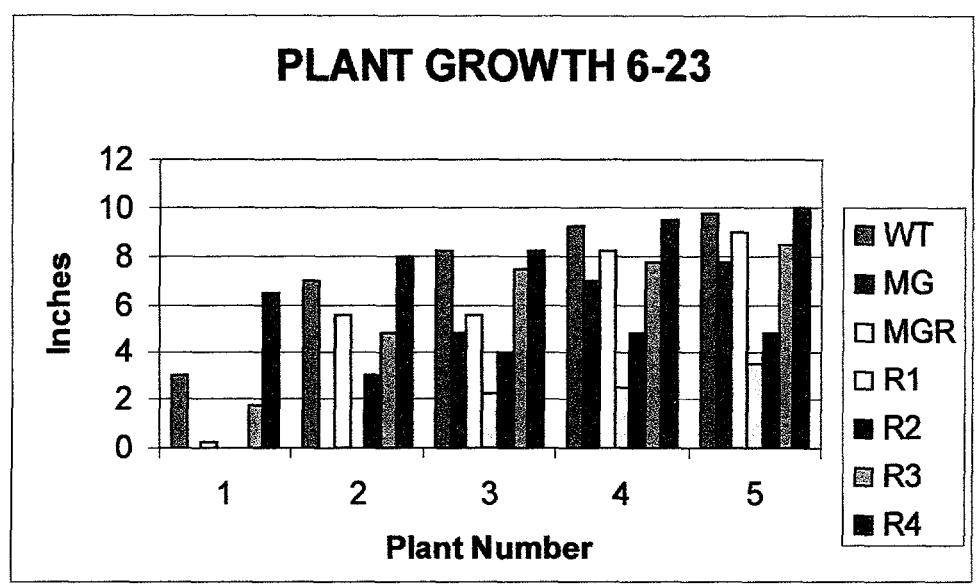
FIG. 1 depicts bar representation of plant growth data following transplantation.

While it is not known which factors are most important for a plant to fully reach it's production potential, it has been found that fertilization with ribose, other pentose sugars, or their derivatives is effective in enhancing both plant growth, yield, hardening, and recovery from their subsequent transplantation process.

Photosynthesis is the process by which green plants and other organisms use light energy to convert carbon dioxide and water into the simple sugar glucose. Plants use much of this glucose, a carbohydrate, as an energy source to build leaves, flowers, fruits, seeds, and hardiness during stress and transplantation. They also convert glucose to cellulose, the structural material used in their cell walls. Most plants produce more glucose than they use, which can be stored in the form of starch and other carbohydrates in their roots, stems, and leaves. The plants can then draw on these reserves for needed extra energy or building materials. As disclosed in U.S. Pat. No. 5,366,954, a storage solution containing 5-deoxy-5-ethylthio-D-ribose (a derivative of ribose) has been found to extend bloom life of a cut flower. Now, it is herein disclosed that, in spite of not fully understanding the mechanisms by which it might operate, it has been discovered that fertilization with ribose and possibly other pentoses and/or their derivatives, alone or in conjunction with other fertilizer ingredients, can enhance a plant's growth, yield, hardening, and its recovery from transplantation.

This invention provides ribose, other pentose sugars, or their derivatives for enhanced plant growth, yield, hardening, and recovery during and following transplantation. This invention also provides ribose in combination with nitrogen, phosphorus, potassium, or any combination of the three. Possible amounts of pentoses: (5 g/1000 mL: 33 mM, 5/500: 66 mM, 51250:132 mM, 5/125: 264 mM).

Ribose is a simple 5-carbon sugar, with a slightly sweet taste. It is a white to light yellow crystalline powder. The amount necessary to have the desired effects on enhanced plant growth can vary with the amount depending on the species of the plant. The ribose can be mixed with water or a liquid fertilizer and applied directly to the soil during the regular watering routine.

For photosynthesis to continue at high rates, the pools of intermediates must be maintained within the chloroplast as the pathway operates as a cycle. At appropriate concentrations, ribose will cause chloroplasts to shrink as a result of exosmosis of water. This volume change brings about a rapid increase in absorbance. There is a fairly fast recovery indicating that exosmosis is followed be endodiffusion of ribose and a consequent increase in turgor within the plant cell.

Photosynthesis can be divided into two separate reactions, the light reaction and the dark reaction. It is in the light reactions that light (light in the range of the red and blue wavelengths have been found to be most effective) creates energy in the form of NADPH and ATP. The NADPH and ATP molecules are then used as the energy source to run the dark reactions.

The dark reactions (commonly called the Calvin Cycle) occur during the daytime and are strictly dependent on the light reactions, i.e., the formation of reductive power as NADPH. Overall, the Calvin Cycle is the process in which carbon is fixed, reduced, and utilized. It is involved in the formation of sugar phosphate intermediates in a cyclic sequence. One complete cycle incorporates three molecules of carbon dioxide and produces one molecule of the three-carbon compound glyceraldehyde-3-phosphate. The fate of glyceraldehyde-3-phosphate is to be converted to starch or exported out of the chloroplast where it is used for the biosynthesis of products needed by the plant.[5]

We have found that the application of ribose, other pentoses, their derivatives, or combinations of pentoses and other nutrients as a fertilizer, preferably every other day in these experiments, over the course of seven days is enough to observe notable differences in plant growth, yield, hardening, and aids in the recovery from transplantation of its species. In order to maintain the gains, it is necessary to continue ribose, other pentoses, their derivatives, or combinations of pentoses and other nutrients must be administrated throughout the period during which is desirable to maintain the continued or improved growth, yield, and hardening alone or following transplantation of the plant. When ribose, other pentoses, their derivatives, or combinations of pentoses and other nutrients as a fertilization medium is discontinued, a slow decline to base line growth rates, yields, hardening, as well as a transplant shock demise ensues.

The fertilizers nitrogen, phosphorus, and potassium when combined with ribose, provides slight incremental improvements over solutions of ribose alone.

The following examples are included to demonstrate the preferred embodiment of the invention. D-ribose is the preferred embodiment, however, to those skilled in the art it is known that certain pentose or pentose derivatives, such as xylitol and ribulose, are readily converted to D-ribose in vivo. Therefore, the term "ribose" is intended to include D-ribose and such precursors thereof and other pentose sugars and derivatives. It should be appreciated by those skilled in the art that the methods and dosages in the examples that follow represent methods and dosages discovered by the inventors to function well in the practice of this invention, and thus can be considered to constitute preferred modes for its practice. However, those skilled in the art should, in light of the present disclosure, appreciate that many changes can be made in the specific embodiments that are disclosed and still obtain a like or similar result without departing from the concept and scope of the invention. All such changes are considered to be within the spirit, scope, and concept of the invention as defined by the appended claims.

EXAMPLE 1

Figure 2:
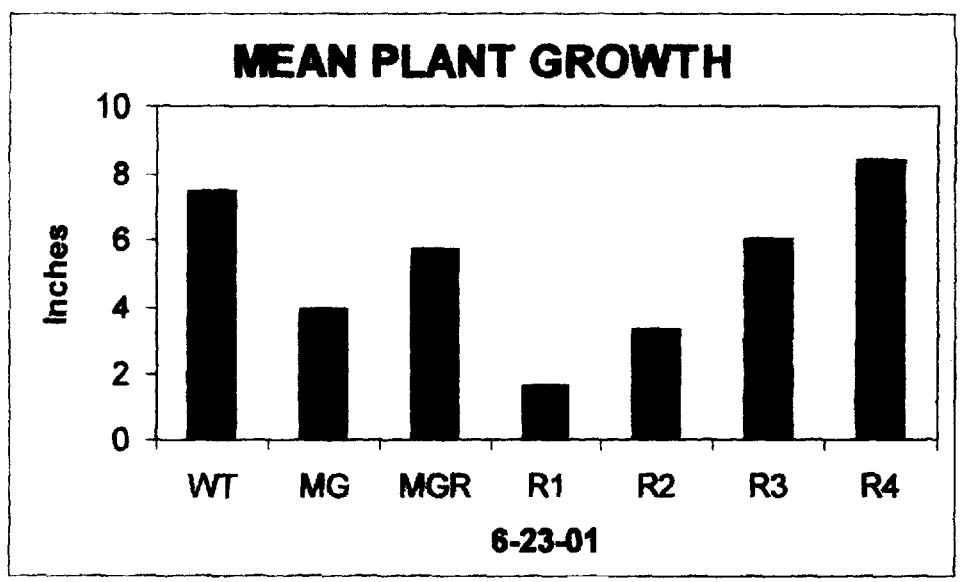
FIG. 2 depicts bar representation of mean plant growth data following transplantation.

Ribose Alone or in Combinations of Other Pentoses, their Derivatives, and Other Fertilizer Components Such as Nitrogen, Phosphorus, or Potassium Aids in the Hardening and Recovery During and Following Transplantation Hosta (H. plantaginea grandiflora) plants were transplanted. The protocol was designed such that half of the plants were supplied with water alone and half of the plants received a ribose based solution, in which powdered D-ribose was mixed in water. All plants were transplanted at the same level in the soil and in like soil. All plants were watered at the same times of day, mid-morning and at dusk. Each plant received the same amount of water/watering (½ liter water at each watering). Table 1 represents plant growth data using various feeding combinations. Table 2 represents plant growth data and hardening following transplantation. Results of plant growth data following transplantation are graphically depicted in FIGS. 1 and 2.

EXAMPLE 2

Plant Growth and Yield

Three different treatments were explored on bean seeds to determine the effects of ribose (at two different doses) on plant growth and proliferation. [The three treatments include control (plain water), a 0.1332 M solution of ribose (5 g D-ribose dissolved in 250 ml water), and a 0.0666 M solution of ribose (5 g D-ribose dissolved in 500 ml water)]. The plants were kept under two different conditions, normal daylight and darkness. A total of six plants will be tested, with the conditions that each plant were tested at listed below.

| Treatments: | |
|---|---|
| Plant 1-5 - placebo, daylight | Plant 4 - placebo, dark |
| Plant 6-10 - 0.1332 M ribose, daylight | Plant 5 - 0.1332 M ribose, dark |
| Plant 3 - 0.0666 M ribose, daylight | Plant 6 - 0.0666 M ribose, dark |

Figure 3:
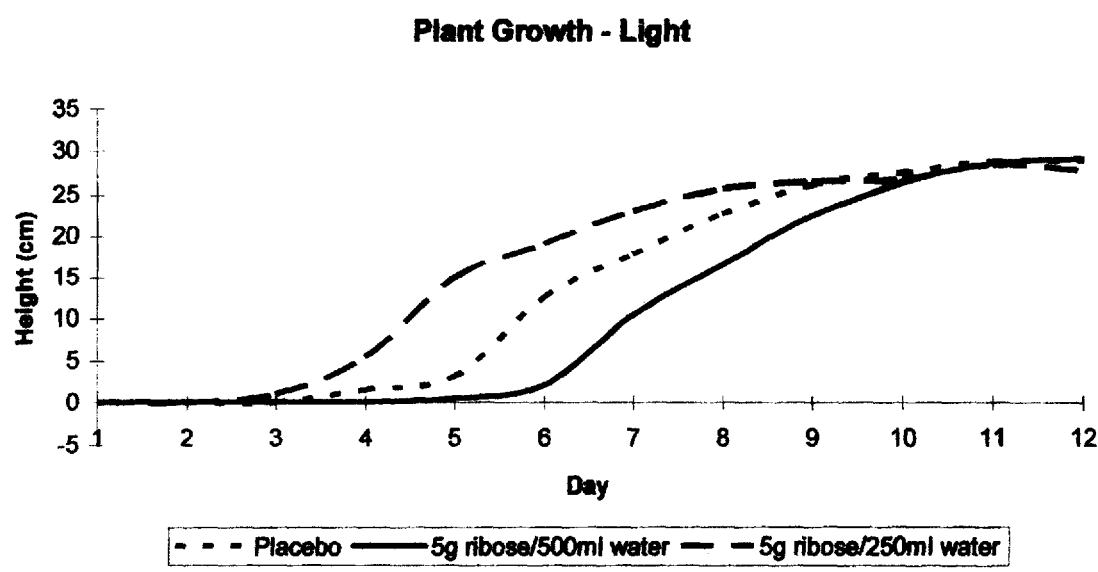
FIG. 3 graphically represents plant growth data during light conditions.
Figure 4:
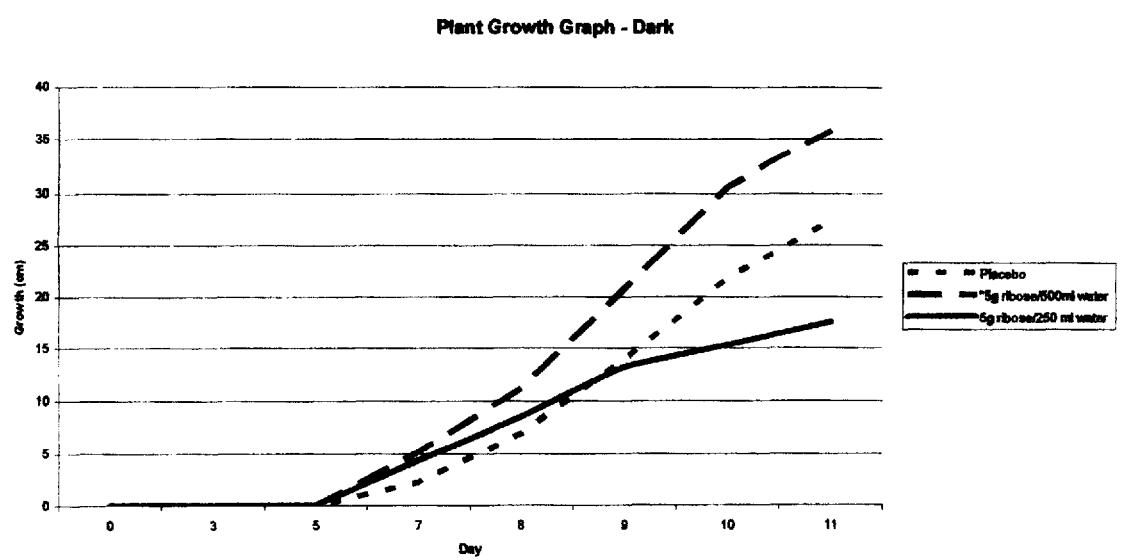
FIG. 4 graphically represents plant growth data during dark conditions.

Each seed was planted under identical conditions (soil and pot size) and all at the same time. The environmental conditions (such as temperature and humidity), except for lighting, were kept constant for all the plants. Once potted, each seed received one to two tablespoons of treatment liquid (as mentioned above). A daily record was kept of the activity of each plant. Watering was done on every other day (or sooner if the soil was deemed too dry by the researcher), each again receiving one tablespoon of treatment liquid. Assessment of the effects of ribose fertilization was determined by measuring the time to the first appearance of a plant from the soil, the rate of growth, and leaf size. Table 3 represents the accumulated plant growth data from Example 2 and FIGS. 3 and 4 are graphic presentations of plant growth during light and dark conditions.

EXAMPLE 3

Root Growth

Often times when trying to grow new plants, stems are cut from the parent plant and placed in water to grow roots before being put in soil. Variable factors and conditions, such as age of the existing plant, diameter and density of the cut stem, can be responsible for the enhanced root growth in one stem from another. Furthermore, obviously new plants can also be grown from seeds or pods planted in soil. The implantation of a seed into soil stabilizes the above mentioned variability. The development of short, thick roots have been shown to aid in a plant's stability, subsequent growth, and ultimate production from the plant.

Identical sized pots, containing the same consistency of soil media, were used in assessing root growth. Bean seeds of similar size were chosen. One seed was planted in each pot. The depth in the soil for each seed that was planted was the same. Paired pots (total of 3 pairs, 6 pots), each containing one bean seed, were used. One pair of pots received 2 teaspoons of water every other day (Group A). The second pair of pots received a low Ribose solution (1 teaspoon of D-ribose in 16 oz of water), each pot received 2 teaspoons of this low dose of Ribose every other day (Group B). The final pair of pots received a higher dose of Ribose (1 teaspoon of D-ribose in 4 oz of water), each pot received 2 teaspoons of this higher dose of Ribose every other day (Group C). In each pair of pots, roots were examined at week 1 and 2, by removing the roots of one pot only in each group at the designed test time point with soil emersion in a bucket of water. At week 2 all remaining pots had shoots emerging from the top soil. The roots were weighed and measured for length. Table 4 reports this data at weeks 1 and 2 following seed implantation. At one week, the Ribose treated seeds had roots that were slightly shorter in length in comparison to the water pots, however, the weight of the Ribose treated roots were heavier than the water treated seeds. This discrepancy expanded when the roots were analyzed at 2 weeks. The low dose Ribose treated roots were thicker, shorter roots, represented by a shorter length and a heavier weight. The high dose Ribose treated roots were thick, however, were less in weight than both the low dose Ribose and water groups. The weight of the roots treated with high dose Ribose were appreciably less in weight than both the water and low dose Ribose treated groups. The water treated roots at 2 weeks demonstrated a thin, spindly, and longer consistency than both the low and high dose Ribose seeds.

EXAMPLE 4

Comparison with other Carbohydrates

Three seeds were planted and watered with one of the three following treatments: water, 0.1332 M D-ribose and water, and 0.1332 dextrose and water. Each seed were planted under identical conditions (soil and pot size) and all at the same time. The environmental conditions (such as temperature and humidity), except for lighting, was kept constant for all the plants. Once potted, each seed received one to two tablespoons of treatment liquid (as mentioned above). A daily record was kept of the activity of each plant. Watering was done on every other day (or sooner if the soil was deemed too dry by the researcher), each again receiving one tablespoon of treatment liquid. Assessment of the effects of ribose fertilization was determined by measuring the time to the first appearance of a plant from the soil, the rate of growth, and leaf size.

EXAMPLE 5

Fertilization with Ribose and Nitrogen

D-ribose plus nitrogen, nitrogen alone, or placebo was administered to bean seeds and measurements of growth and yield was made as in Example 2.

EXAMPLE 6

Fertilization with Ribose and Phosphorus

D-ribose plus phosphorus, phosphorus alone, or placebo was administered to bean seeds and measurements of growth and yield was made as in Example 2.

EXAMPLE 7

Fertilization with Ribose and Potassium

D-ribose plus potassium, potassium alone, or placebo was administered to bean seeds and measurements of growth and yield was made as in Example 2.

EXAMPLE 8

Fertilization: Ribose and Combination of Nitrogen, Phosphorus, and Potassium

D-ribose plus the combination, the combination alone, or placebo was administered to bean seeds and measurements of growth and yield was made as in Example 2.

All of the compositions and methods disclosed and claimed herein can be made and executed without undue experimentation in light of the present disclosure. While the compositions and methods have been described in terms of preferred embodiments, it will be apparent to those skilled in the art that variations may be applied to the compositions and methods described herein without departing from the concept and scope of the invention.

REFERENCES

[1] Elsheikh E A, A A Elzidany. Effects of Rhizobium inoculation, organic and chemical fertilizers on yield and physical properties of faba bean seeds. *Plant Foods Hum Nutr.* 1997; 51(2): 137-144.

[2] Omer E A, A Fattah, M Razin, S S Ahmed. Effect of cutting, phosphorus and potassium fertilization on guar plant (*Cyamoposis tetragonoloba*) in newly reclaimed soil in Egypt. *Plant Foods Hum Nutr.* 1993 November; 44(3): 277-284.

[3] Tinus R W. Relationship between carbohydrate concentration and root growth potential in coniferous seedlings from three climates during cold hardening and dehardening. *Tree Physiology.* 2000 October; 20(16): 1097-1104.

[4] Huner N P, F D Macdowall. The effects of low temperature acclimation of winter rye on catalytic properties of its ribulose bisphosphate carboxylase-oxygenase. *Can J Biochem.* 1979 July; 57(7): 1036-1041.

[5] "Photosynthesis," Microsoft® Encarta® Online Encyclopedia 2001.

TABLE 1

Plant feeding with ribose for growth

Planting date: 4 June 5 seeds per plot
Ribose from container #1, opened on 4 Jun. 2001
Each seed/plant receives 2 tablespoons every other day of the week (3× per week)
Plots rotated weekly to minimize location influence
Measured to the Y
Water = WT
Miracle Grow ™ = MG
Miracle grow ™ plus stock ribose = MGR
Ribose 1: 1 teaspoon ribose per 4 oz water (stock solution) = R1
Ribose 2: cut stock in half with water = R2
Ribose 3: cut ribose #2 in half with water = R3
Ribose 4: cut ribose #3 in half with water = R4
W: Wilted and died
Sprout 11 June all plots
Measured in inches
Plant measures taken 23 June

| Plant # | WT | MG | MGR | R1 | R2 | R3 | R4 |
|---|---|---|---|---|---|---|---|
| 1 | 3 | 0 | 0.25 | 0 | 0 | 1.75 | 6.5 |
| 2 | 7 | 0 | 5.5 | 0 | 3 | 4.75 | 8 |
| 3 | 8.25 | 4.75 | 5.5 | 2.25 | 4 | 7.5 | 8.25 |
| 4 | 9.25 | 7 | 8.25 | 2.5 | 4.75 | 7.75 | 9.5 |
| 5 | 9.75 | 7.75 | 9 | 3.5 | 4.75 | 8.5 | 10 |
| Mean | 7.45 | 3.9 | 5.7 | 1.65 | 3.3 | 6.05 | 8.45 |
| STD | 2.7 | 3.7 | 3.4 | 1.6 | 2.0 | 2.8 | 1.4 |
| Unsprouted | 0 | 2 | 0 | 2 | 1 | 0 | 0 |

Measured 8 July

| | | | | | | | |
|---|---|---|---|---|---|---|---|
| 1 | W | 0 | 0 | 0 | 0 | 3.5 | 8.75 |
| 2 | 8.5 | 0 | 7 | 0 | 4.25 | 6.5 | 10 |
| 3 | 9 | 6.5 | 6.75 | 3 | 5.5 | 9.75 | 10.5 |
| 4 | 11 | 9 | 10 | 3.75 | 6.5 | 10 | 11.75 |
| 5 | 11.25 | 8.75 | 10.25 | 4.75 | 6.75 | 10.75 | 12 |
| Mean | 9.9 | 6.1 | 8.5 | 2.9 | 5.8 | 9.3 | 11.1 |
| STD | 1.4 | 4.2 | 1.9 | 2.0 | 1.1 | 1.9 | 1.0 |
| #Plants/blossom | 2 | 1 | 2 | 1 | 3 | 4 | 5 |

TABLE 2

TRANSPLANTS IN GARDEN WITH BEANS (B) AND KOHLRABI (K)
(plant order from left to right in plot)
Bean measures to Y = total height: 9*20 would be 9 cm to the Y and 25 cm overall height; W: Wilt and died measures were made before moving/29 Sep was first measure after transplant
Feedings (2T) took place on Monday, Wednesday, Friday
Miracle Grow feeding took place on every other Monday with water given to those plants on Wed and Fri

| | B | B | B | K | K | K | K |
|---|---|---|---|---|---|---|---|
| WATER | | | | | | | |
| 9-Sep | 8*25 | 10*26 | 8*23 | 11 | 14 | 10 | 13 |
| 29-Sep | 9.75*27 | 10.5*27 | 10*25 | W | 14 | 11 | 16 |
| 19-Oct | 10*28 | 10.5*28 | 11*27 | 0 | 15 | 11 | 17 |
| 1-Nov | 10*28 | 11*28.5 | 11*27 | 0 | 16 | 11 | 18 |
| MG | | | | | | | |
| 9-Sep | 9*27 | 7*20 | 8*21 | 9*25 | 12 | 14 | 9 |
| 29-Sep | 10*29 | 8.5*22 | 9*22 | W | 14 | 16 | 13 |
| 19-Oct | 11*30 | 9*22.5 | 10*23 | W | 15 | 16 | 13 |
| 1-Nov | 11*30.5 | 9*23 | 10.5*24 | W | 15.5 | 17 | 13 |
| LOW RIB (R4) | | | | | | | |
| 9-Sep | 6*21 | 8*22 | 12 | 13 | 17 | 17 | 11 |
| 29-Sep | 7.5*24 | 10.5*26 | 14 | 16 | 19 | 19.5 | 13 |
| 19-Oct | 8.75*26 | 12*28 | 15 | 18 | 19.5 | 20 | 14.5 |
| 1-Nov | 10*27 | 13*30 | 16.5 | 19 | 22 | 21 | 15 |
| HIGH RIB (R1) | | | | | | | |
| 9-Sep | 9*24 | 10*26 | 6*11 | 4 | 9 | 6 | 13 |
| 29-Sep | W | 14*30 | 9.5*14 | 7 | 13 | 7 | 17 |
| 19-Oct | W | 16*32 | 10*15 | 9.5 | 14.5 | 8 | 17.5 |
| 1-Nov | W | 17*33.5 | 12*18 | 11 | 15.5 | 9.8 | 18 |

***NOTE:
Keep in mind that Oct there was frost and that daylight hours are shortening

TABLE 3

PLANT GROWTH-HEIGHT

| | 17-Sep | 20-Sep | 22-Sep | 24-Sep | 25-Sep | 26-Sep | 27-Sep | 28-Sep | 29-Sep | 30-Sep | 3-Oct | 6-Oct |
|---|---|---|---|---|---|---|---|---|---|---|---|---|
| Day | 0 | 3 | 5 | 7 | 8 | 9 | 10 | 11 | 12 | 13 | 16 | 19 |
| Placebo - Light | 0 | 0 | 0 | 1.6 | 3.2 | 12.6 | 17.8 | 22.8 | 26.1 | 27.4 | 28.7 | 28.7 |
| 5/500 - Light | 0 | 0 | 0 | 0 | 0.5 | 2.1 | 10.5 | 16.6 | 22.5 | 26.3 | 28.4 | 29 |
| 5/250 - Light | 0 | 0 | 1.1 | 5.5 | 15 | 19.1 | 23.1 | 25.7 | 26.4 | 26.6 | 28.3 | 27.6 |
| Placebo - Dark | 0 | 0 | 0 | 2.3 | 6.9 | 13.9 | 21.8 | 27.3 | 30.8 | 34.3 | 36.3 | 36.7 |
| 5/500 - Dark | 0 | 0 | 0 | 5.2 | 11.1 | 20.8 | 30.6 | 35.8 | 39.3 | 44.8 | 46.8 | 46.8 |
| 5/250 - Dark | 0 | 0 | 0 | 4.4 | 8.5 | 13.2 | 15.3 | 17.6 | 19.6 | 21.1 | 24.7 | |

TABLE 3-continued

PLANT GROWTH-HEIGHT

| | | 17-Sep | 20-Sep | 22-Sep | 24-Sep | 25-Sep | 26-Sep | 27-Sep | 28-Sep | 29-Sep | 30-Sep | 3-Oct | 6-Oct |
|---|---|---|---|---|---|---|---|---|---|---|---|---|---|
| Amount of Growth | Between Measurements | | | | | | | | | | | | |
| Placebo - Light | | 0 | 0 | 0 | 1.6 | 1.6 | 9.4 | 5.2 | 5 | 3.3 | 1.3 | 1.3 | 0 |
| 5/500 - Light | | 0 | 0 | 0 | 0 | 0.5 | 1.6 | 8.4 | 6.1 | 5.9 | 3.8 | 2.1 | 0.6 |
| 5/250 - Light | | 0 | 0 | 1.1 | 4.4 | 9.5 | 4.1 | 4 | 2.6 | 0.7 | 0.2 | 1.7 | -0.7 |
| Placebo - Dark | | 0 | 0 | 0 | 2.3 | 4.6 | 7 | 7.9 | 5.5 | 3.5 | 3.5 | 2 | 0.4 |
| 5/500 - Dark | | 0 | 0 | 0 | 5.2 | 5.9 | 9.7 | 9.8 | 5.2 | 3.5 | 5.5 | 2 | 0 |
| 5/250 - Dark | | 0 | 0 | 0 | 4.4 | 4.1 | 4.7 | 2.1 | 2.3 | 2 | 1.5 | 3.6 | |
| Rate of Growth | Between Measurements | | | | | | | | | | | | |
| Placebo - Light | | 0 | 0 | 0 | 0.80 | 1.60 | 9.40 | 5.20 | 5.00 | 3.30 | 1.30 | 0.43 | 0.00 |
| 5/500 - Light | | 0 | 0 | 0 | 0 | 0.50 | 1.60 | 8.40 | 6.10 | 5.90 | 3.80 | 0.70 | 0.20 |
| 5/250 - Light | | 0 | 0 | 0.55 | 2.20 | 9.50 | 4.10 | 4.00 | 2.60 | 0.70 | 0.20 | 0.57 | -0.23 |
| Placebo - Dark | | 0 | 0 | 0 | 1.15 | 4.60 | 7.00 | 7.90 | 5.50 | 3.50 | 3.50 | 0.67 | 0.13 |
| 5/500 - Dark | | 0 | 0 | 0 | 2.60 | 5.90 | 9.70 | 9.80 | 5.20 | 3.50 | 5.50 | 0.67 | 0.00 |
| 5/250 - Dark | | 0 | 0 | 0 | 2.20 | 4.10 | 4.70 | 2.10 | 2.30 | 2.00 | 1.50 | 1.20 | |
| Rate of Growth | Overall Thru Date | | | | | | | | | | | | |
| Placebo-Light | | | | 0 | 0.23 | 0.40 | 1.40 | 1.78 | 2.07 | 2.18 | 2.11 | 1.79 | 1.51 |
| 5/500 - Light | | | | 0 | 0.00 | 0.06 | 0.23 | 1.05 | 1.51 | 1.88 | 2.02 | 1.78 | 1.53 |
| 5/250 - Light | | | | 0.22 | 0.79 | 1.88 | 2.12 | 2.31 | 2.34 | 2.20 | 2.05 | 1.77 | 1.45 |
| Placebo - Dark | | | | 0 | 0.33 | 0.86 | 1.54 | 2.18 | 2.48 | 2.57 | 2.64 | 2.27 | 1.93 |
| 5/500 - Dark | | | | 0 | 0.74 | 1.39 | 2.31 | 3.06 | 3.25 | 3.28 | 3.45 | 2.93 | 2.46 |
| 5/250 - Dark | | | | 0 | 0.63 | 1.06 | 1.47 | 1.53 | 1.60 | 1.63 | 1.62 | 1.54 | |

R = ribose, Placebo = tap water

TABLE 4

ROOT GROWTH ASSESSMENT

| | Weight (gm) | Length (cm) |
|---|---|---|
| Week 1 | | |
| Water | 1.32 | 14.6 |
| Low Ribose | 1.55 | 13.4 |
| High Ribose | 1.46 | 13.8 |
| Week 2 ** | | |
| Water | 0.57 | 22.8 |
| Low Ribose | 1.01 | 16.0 |
| High Ribose | 0.26 | 14.7 |

** The week 2 plants were cut off at the point where the plant was above the soil, so literally just the roots were weighed.
LEGEND: Water - 2 Tbsp of water every other day; Low Ribose - 2 Tbsp every other day (1 tsp ribose in 16 oz of water); High Ribose - 2 Tbsp every other day (1 tsp ribose in 4 oz of water)

We claim:

1. A method to treat plants consisting of the topical application of a solution of a pentose comprising 1.25 to 5 grams of the pentose dissolved in 250 milliliters of water to the roots of the plants, wherein the pentose is D-ribose, and whereby the hardiness and growth of the plants is enhanced.

2. The method of claim 1 wherein the solution is applied once to three times daily.

3. The method of claim 2 wherein the solution is applied for at least one week, whereby the weight of plant roots is increased.

4. A method to treat plants exhibiting transplant shock incidence, the method comprising applying a solution of a pentose comprising 1.25 to 5 grams of the pentose dissolved in 250 milliliters of water to the roots of the plants exhibiting transplant shock incidence, wherein the pentose is D-ribose.

5. The method of claim 4, wherein applying comprises topically applying a solution of D-ribose to the roots of the plants.

6. A method to treat plants following transplantation, the method comprising applying a solution of a pentose comprising 1.25 to 5 grams of the pentose dissolved in 250 milliliters of water to the roots of the plants following transplantation, wherein the pentose is D-ribose.

7. The method of claim 6, wherein applying comprises topically applying a solution of D-ribose to the roots of the plants.

8. A method to treat plants, the method comprising applying a solution of a pentose comprising 1.25 to 5 grams of the pentose dissolved in 250 milliliters of water to the seeds of the plants, wherein the pentose is D-ribose.

9. The method of claim 8, wherein applying comprises topically applying a solution of D-ribose to the seeds of the plants.

10. A method to treat plants to enhance hardiness and growth of the plants, the method comprising applying a solution of a pentose comprising 1.25 to 5 grams of the pentose dissolved in 250 milliliters of water to the roots of the plants throughout the period during which the enhanced hardiness and growth is desired, wherein the ribose is D-ribose.

11. The method of claim 8, wherein applying the solution of D-ribose to the seeds of the plants aids in the germination of the seeds.

12. The method of claim 8 wherein applying the solution of D-ribose to the seeds of the plants affects the growth pattern of the germinated seeds.

* * * * *